United States Patent [19]
Burke et al.

[11] Patent Number: 5,786,139
[45] Date of Patent: Jul. 28, 1998

[54] METHOD AND KIT FOR DETECTING NUCLEIC ACID CLEAVAGE UTILIZING A COVALENTLY ATTACHED FLUORESCENT TAG

[75] Inventors: Thomas J. Burke, Madison; Randall E. Bolger, Oregon; William J. Checovich, Madison; David V. Thompson, Monona, all of Wis.

[73] Assignee: PanVera Corporation, Madison, Wis.

[21] Appl. No.: 353,079

[22] Filed: Dec. 9, 1994

[51] Int. Cl.[6] .............................. C12Q 1/68; C12N 9/16; C07H 21/00
[52] U.S. Cl. .......................... 435/6; 435/196; 536/25.32
[58] Field of Search .......................... 435/6, 7.72, 196; 536/25.32

[56] References Cited

U.S. PATENT DOCUMENTS

| | | | |
|---|---|---|---|
| 4,681,859 | 7/1987 | Kramer | 436/501 |
| 4,751,190 | 6/1988 | Chiapetta et al. | 436/546 |
| 4,902,630 | 2/1990 | Bennett et al. | 436/546 |
| 5,210,015 | 5/1993 | Gelfand et al. | 435/6 |

FOREIGN PATENT DOCUMENTS

WO 92/18650  10/1992  WIPO .............................. C12Q 1/68

OTHER PUBLICATIONS

Yonemura et al. A new assay method for DNase by fluorescence polarization and flourescence intensity using DNA–ethidium bromide complex as a sensitive substrate. J. Biochem. vol. 92 1297–1303, 1982.

Wiegant et al. In situ hybridization with flouresceinated DNA Nucl. Acids Res. vol. 19 3237–3241, 1991.

Applied Biosystems Inc. Catalog 101–134, 1993.

Berkower et al. Isolation and characterization of an endonuclease from *Escherichia coil* specific for ribonucleic acid in ribonecleic deoxyribonucleic hybrid structures J. Biol. Chem. vol. 248 5914–5921, 1973.

Eron et al. Inhibition of deoxyribonuclease action by actinomycin D and ethidium bromide Biochim. Biophys. Acta vol. 114 633–636, 1966.

Kim, Ug–Sung et al., "Dynamics and Structures of DNA: Long–Range Effects of a 16 Base–Pair $(CG)_8$ Sequence on Secondary Structure." *Biopolymers* 1993; 33: 1725–45.

Paoletti, J. et al., "The Structure of Chromatin; Interaction of Ethidium Bromide with Native and Denatured Chromatin." *Biochemistry* 1977; 16: 351–357.

*Primary Examiner*—James Ketter
*Assistant Examiner*—John S. Brusca
*Attorney, Agent, or Firm*—Mark K. Johnson

[57] ABSTRACT

The present invention is based on the degradation of a fluorescence labeled nucleic acid such as DNA (F-DNA), RNA (F-RNA) or DNA/RNA substrate. The label may be covalently attached to the relatively high volume substrate at one position or many positions. The nucleic acid is then put in contact with another substance and activity is detected by Fluorescence Polarization.

16 Claims, 5 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear     ( i i ) MOLECULE TYPE: oligonucleotide     ( i i i ) HYPOTHETICAL: yes     ( x i ) SEQUENCE DESCRIPTION: SEQ ID NO:1:

ATCGAACTAG TTAACTAGTA CGCAA 25

( 2 ) INFORMATION FOR SEQ ID NO:2:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear     ( i i ) MOLECULE TYPE: oligonucleotide     ( i i i ) HYPOTHETICAL: yes     ( x i ) SEQUENCE DESCRIPTION: SEQ ID NO:2:

GCATCAGATT AGAGCTGATG CCTCCGGTCA CTGTCACCCA ACCCATCTTA 50

( 2 ) INFORMATION FOR SEQ ID NO:3:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear     ( i i ) MOLECULE TYPE: oligonucleotide     ( i i i ) HYPOTHETICAL: yes     ( x i ) SEQUENCE DESCRIPTION: SEQ ID NO:3:

GATCCTCGTT TTAAGAACAG TTTGTAACCA AAGATC 36

( 2 ) INFORMATION FOR SEQ ID NO:4:

( i ) SEQUENCE CHARACTERISTICS:

(A) LENGTH: 33 bases
(B) TYPE: nucleic acid
(C) STRANDEDNESS: single
(D) TOPOLOGY: linear (i i) MOLECULE TYPE: oligonucleotide (i i i) HYPOTHETICAL: yes (x i) SEQUENCE DESCRIPTION: SEQ ID NO:4:

GATCTCTGGT CAGGTTGTGA AATCACAACT GTG  33

(2) INFORMATION FOR SEQ ID NO:5:

(i) SEQUENCE CHARACTERISTICS:
(A) LENGTH: 20 bases
(B) TYPE: nucleic acid
(C) STRANDEDNESS: single
(D) TOPOLOGY: linear (i i) MOLECULE TYPE: oligonucleotide (i i i) HYPOTHETICAL: yes (x i) SEQUENCE DESCRIPTION: SEQ ID NO:5:

ATTGAAGCAT TTATCAGGGT  20

METHOD AND KIT FOR DETECTING NUCLEIC ACID CLEAVAGE UTILIZING A COVALENTLY ATTACHED FLUORESCENT TAG

FIELD

The present invention relates generally to a method and kit for detecting nucleic acid cleavage utilizing a covalently attached fluorescent tag. The present invention particularly relates to fluorescence polarization (FP) assays which detect enzyme and chemical cleavage of covalently labeled DNA, RNA and RNA/DNA hybrids.

BACKGROUND

In the laboratory, recombinant molecules are created by cleaving one nucleic acid segment and pasting it to another segment. Nucleases are the fundamental cellular and viral enzymes that cleave nucleic acids. As a laboratory tool, nucleases are purified to perform in a repeatable and predictable manner. Removal of contaminants is paramount to insure that nuclease activity is well defined. Conversely, nucleases are contaminents in other biological assays.

Historically, assays involving nucleases have been tedious, time-consuming and dangerous, often requiring radioactive labeling. Nucleases such as RNases and DNases have specificities, charges and sizes that vary widely. If a reagent is contaminated by an unwanted RNase, the source of the contamination can be difficult to identify, and, as a result, an entire stock of reagents may be thrown out in an attempt to be rid of the RNase. Even ultrapure grades of commercial proteins contain trace amounts of unwanted RNase. In some laboratory work, specific DNase activity measurements may be required to be verified or, in another example, DNase contamination similar to the RNase contamination described must be identified.

Fluorescence polarization was first described in 1926 by Perrin F., "Polarization de la lumiere de fluorescence vie moyenne des molecules dans l'etat excite", J Phys Rad 7: 390–401 (1926). Fluorescence polarization assay techniques are based on the principle that a fluorescence labeled compound will emit fluorescence when excited by plane polarized light, having a degree of polarization inversely related to its rate of rotation. If the labeled molecule remains stationary throughout the excited state it will emit light in the same polarized plane; if it rotates while excited, the light emitted is in a different plane. Specifically, when a large labeled molecule is excited by plane polarized light, the emitted light remains highly polarized because the fluorophore is constrained (by its size) from rotating between light absorption and fluorescent light emission. When a smaller molecule is excited by plane polarized light, its rotation is much faster than the large molecule and the emitted light is more depolarized. Polarization is related to the time it takes a fluorescence labeled molecule to rotate through an angle of approximately 68.5 degrees: designated the correlation time. Correlation time is related to viscosity, absolute temperature and molecular volume. If viscosity and temperature are held constant, correlation time, and therefore, polarization, are directly proportional to the molecular volume. Changes in molecular volume may be due to molecular binding, dissociation, synthesis, degradation, or conformational changes of the fluorescence labeled molecule. Accordingly, when plane polarized light is passed through a solution containing a relatively high molecular weight fluorescence labeled compound, the degree of polarization of the emitted light will, in general, be greater than when plane polarized light is passed through a solution containing a relatively low molecular weight fluorescence labeled compound.

The term "Fluorescence polarization" (P) is defined as:

$$P = \frac{\text{Parallel Intensity} - \text{Perpendicular Intensity}}{\text{Parallel Intensity} + \text{Perpendicular Intensity}}$$

Parallel Intensity is the intensity of the emission light parallel to the excitation light plane and Perpendicular Intensity is the intensity of the emission light perpendicular to the excitation light plane. Since P is a ratio of light intensities, it is a dimensionless number and has a maximum value of 0.5 for fluorescein.

Fluorescence anisotropy (A) is another term commonly used to describe this phenomenon; however, it is related fluorescence polarization according to the following formula:

$$A = \frac{2P}{3 - P}$$

An example which utilizes fluorescence polarization techniques is U.S. Pat. No. 4,681,859 granted to Kramer. The patent describes an immunoassay for detecting the presence of large molecular weight aqueous ligands. U.S. Pat. Nos. 4,751,190 granted to Chiapetta et.al. and 4,902,630 granted to Bennett et.al. describe fluorescence polarization techniques involving immunoassays with proteins. International Publication No. WO 92/18650 describes a method for detecting amplified RNA or DNA complementary target sequences by fluorescence labeling RNA or DNA probes to show increased polarization when the probes are hybridized to target sequences. A fluorescence polarization method as applied to DNase is described in Yonemura et.al., "A New Assay Method for DNase by Fluorescence Polarization and Fluorescence Intensity Using DNA-Ethidium Bromide Complex as a Sensitive Substrate", J. Biochem. 92, 1297–1303 (1982). Here, ethidium bromide is utilized as the fluorescent label, intercalating with DNA by dipole-dipole and electrostatic forces.

Although the prior art methods described have been useful, they contain certain disadvantages. Generally, when working with nucleases, a metal cofactor, such as magnesium or calcium, is required. These metal ions may prevent, and certainly interfere with, intercalating dyes like ethidium bromide from binding to DNA. Furthermore, high concentrations of fluorescent dye (500 nanomolar) and DNA (5 micrograms/ml) are required. At lower concentrations, the dye and DNA do not bind to each other; especially in the presence of metal ions. Moreover, ethidium bromide does not covalently bind DNA, rather, its mechanism is an equilibrium binding. This means that as DNA and ethidium bromide solutions are diluted, the two reagents come apart. Many reagents such as detergents, ionic salts, buffers, nucleotides and proteins can have a significant negative effect on equilibrium binding. Single-stranded RNA folds on itself and becomes more double stranded as the concentration of salt increases. When this intra-strand hybridization occurs, more intercalating dye may ionically position itself adjacent the double-stranded bases causing more polarization, thus, inversely affecting detection.

SUMMARY

The method of detecting cleavage of a nucleic acid comprising, covalently attaching at least one fluorescence emitting label to the nucleic acid to be cleaved; incubating the labeled nucleic acid of step (a) with a reagent to be tested; and, measuring the fluorescence polarization of the label.

The method of detecting cleavage of a nucleic acid comprising covalently attaching a fluorescence emitting label to the nucleic acid; mixing a reagent to be tested with the labeled nucleic acid; incubating the mixture of step (b) for a time sufficient for the reagent to react with the nucleic acid; and, measuring the degree of fluorescence polarization of the label.

A kit for detecting cleavage of nucleic acids comprising a receptacle containing a nucleic acid labeled with a fluorescence emitting tag; and instructions for use.

The present invention provides assays wherein metal cofactors (i.e., magnesium or calcium) in solution with a nuclease do not interfere with sensitivity of detection since the fluorescent tag is covalently attached to the nucleic acid; a high concentration of metal ion will not dislodge the tag. By covalently attaching the fluorescent tag, very small amounts ($50 \times 10^{-12}$ molar) of nucleic acid may be utilized increasing the sensitivity of detection in this method.

Other objects, features and advantages of the present invention will become apparent from the following detailed description and the specific examples, while indicating preferred embodiments of the invention, are given by way of illustration only, since various changes and modifications within the spirit and scope of the invention will become apparent to those skilled in the art.

DETAILED DESCRIPTION OF THE PREFERRED EMBODIMENTS

Definitions

The term "nucleotide" is a term of art that refers to a base-sugar-phosphate combination. Nucleotides are the monomeric units of nucleic acid polymers (DNA and RNA). The term includes ribonucleoside triphosphates, such as ATP, CTP, GTP, or UTP, and deoxyribonucleotide triphosphates, such as dATP, dCTP, dGTP, or dTTP. Included in this definition are modified nucleotides which include additions to the sugar- phosphate as well as to the bases. Examples of such modifications include a sulphur molecule substituted for a phosphate and a fluoride substituted for a hydroxyl on the sugar ring.

The term "nucleic acid" is defined as multiple nucleotides attached in the form of a single or double stranded polynucleotide that can be natural; or derived synthetically, enzymatically, and by cloning methods. This definintion also includes modification such as replacing the sugar phosphate backbone with a synthesized protein-like amide structure.

The term "nucleic acid cleaving substance" refers to any nucleic acid reactant that chemically cleaves the nucleic acid.

The term "nuclease" refers to enzymes that hydrolyze the phosphodiester bonds of nucleic acids. The nucleases that are specific for RNA are called ribonucleases (RNases). The nucleases that are specific for DNA are called deoxyribonucleases. (DNases). A few of the nucleases lack any degree of specificity and hydrolyze the phosphodiester bonds of both DNA and RNA. Those nucleases that attack the polynucleotide chain at either the 5' or 3' terminus are known as exonucleases; those that attack within the chain are called endonucleases.

The terms "DNase" and "RNase" are defined as nucleases that associate with and cleave DNA and RNA, respectively, forming oligonucleotide fragments and individual nucleotides. Some nucleases cleave with no specificity; some preferentially attack at a purine or pyrimidine nucleotide residue; while others (such as restriction enzymes or integrases) cleave within selected sequences. One can determine whether or not a particular nuclease is suitable for the present invention by comparing the candidate nuclease with nucleases listed below and illustrated in the Examples. The following Examples include, but are not limited to, DNase I (generally cleaves between any bases), Exonuclease III (cleaves from 3' end) and Hinc II and Bam HI (restriction enzymes). Examples of RNases include, but are not limited to, RNase A, RNase T1 and RNase H.

The terms "fragment" and "oligonucleotide" may be used interchangeably in this application, each being a polynucleotide. Fragment specifically refers to any subject sequence from a nucleic acid having a base sequence less than that of the starting nucleic acid material. Oligonucleotide refers herein to a polynucleotide of less than 75 nucleotides.

The term fluorescent "derivative" refers to a compound incorporating fluorescence emitting properties such that the requisite activity is maintained.

The term fluorescent "analog" includes any compound having fluorescent characteristics. One can determine whether or not a particular fluorescence emitting compound is suitable for the present invention by comparing the candidate compound with successful compounds listed below and illustrated in the Examples. If the candidate compound performs a required function such that a successful detection can be obtained, similar to the compounds used in this application, the compound is suitable for use with this invention. Fluorescein is covalently attached in the preferred embodiments, however, other fluorescence emitting compounds for potential use in the present invention include rhodamine, texas red and lucifer yellow.

Suitable fluorescein labels for use in the invention include, for example, fluorescein-maleimide, fluorescein-iodoacetamide, 5-bromomethyl-fluorescein, fluorescein-succinimidyl ester (FS), fluorescein-C6-succinimidyl ester (FXS), carboxy-fluorescence fluorescein isothiocynates (FITC), triazinylaminofluoresceins (DTAF) and many other labels well known in the art.

General Description

The present invention is based on the degradation of a fluorescence labeled nucleic acid such as DNA (F-DNA), RNA (F-RNA) or DNA/RNA substrate. The label may be covalently attached to the relatively high volume substrate at one position or many positions. In solution, fluorescein, which is covalently attached to the nucleic acid substrate, is excited by plane polarized light. Fluorescein emits light in this excited state that is more polarized than free fluorescein; primarily due to the slow rotation of the substrate. As the F-labeled substrate encounters a cleaving protein such as a nuclease that may be present, it is hydrolyzed to smaller fragments which rotate at a greater speed, depolarizing the fluorescein emitted light.

F – NUCLEICACID $\xrightarrow{\text{CLEAVING ENZYME}}$ F – NUCLEOTIDES
          F – FRAGMENTS
(HIGH POLARIZATION)   (LOW POLARIZATION)

The emitted light is measured and quantitated by a detector which indicates that the fluorescence polarization value has decreased to less than the value prior to the introduction of a nuclease, demonstrating cleavage. Detection is performed by a fluorescence polarimeter with a sensitivity sufficient to detect less than 20 picomolar fluorescein in the polarization mode, such as the Beacon™ fluorescence polarization analyzer (PanVera Corp., Madison, Wis.).

DNA, RNA and DNA/RNA hybrids may be labeled in 1 of 3 ways, in the preferred embodiment:

1) during the chemical synthesis of the oligonucleotide;

2) as a post-synthetic modification of the oligonucleotide; and,

3) Enzymatic synthesis or modification of nucleic acid where a fluorescent nucleotide is incorporated into the polynucleotide or oligonucleotide.

The primary drawback to employing step 3 is that long (6 to 21-carbon for RNA; 1 to 12-carbon for DNA) carbon chains or "spacer arms" are required to attach reactive amides to the oligonucleotide. Chemical synthesis of a modified oligonuleotide has two primary advantages. Fluorescein-labeled bases are available with small (1 to 6-carbon) spacer arms that successfully limit the rotational freedom of the fluorescein molecule. The base attached to small spacer arms can be substituted for the natural analog anywhere along the oligonucleotide sequence. In this way, the single-stranded oligonucleotide can be labeled with a single fluorescein on one end of the molecule, thereby limiting the interfering stearic hindrance associated with fluorescein attached with a long spacer arm.

In one preferred embodiment, fluorescein is covalently attached to an oligonucleotide probe through an aminochlorotriazinylaminoalkyphosphoryl group having the generalized structure:

wherein n is an integer from 1 to about 21 (the attachment is referred to as DTAF). Another example of fluorescein attachment is shown below:

Example of 6 C attachment

FLUORESCEIN

The present invention provides for nucleic acid cleaving kits having a receptacle for each of the following in sufficient amounts to perform the following examples:
1) Fluorescein labeled nucleic acid
2) Instructions for use By the term "instructions for use," it is meant a tangible expression describing the reagent concentration for at least one assay method, parameters such as the relative amount of reagent and sample to be admixed, maintenance time periods for reagent/sample admixtures, temperature, buffer conditions and the like.

EXAMPLE 1
Restriction Enzyme Cleavage of DNA

Two oligonucleotides were synthesized by Eppendorf (Madison, Wis.) using standard phosphoramidite chemistry for use in an embodiment of the invention. The two 25 base complementary strands include the 6 base recognition sequence for Hinc II:

```
5'-Fluorescein—GTTAAC-3'
              ||||||
          3'-CAATTG-5'
```

Figure 1:
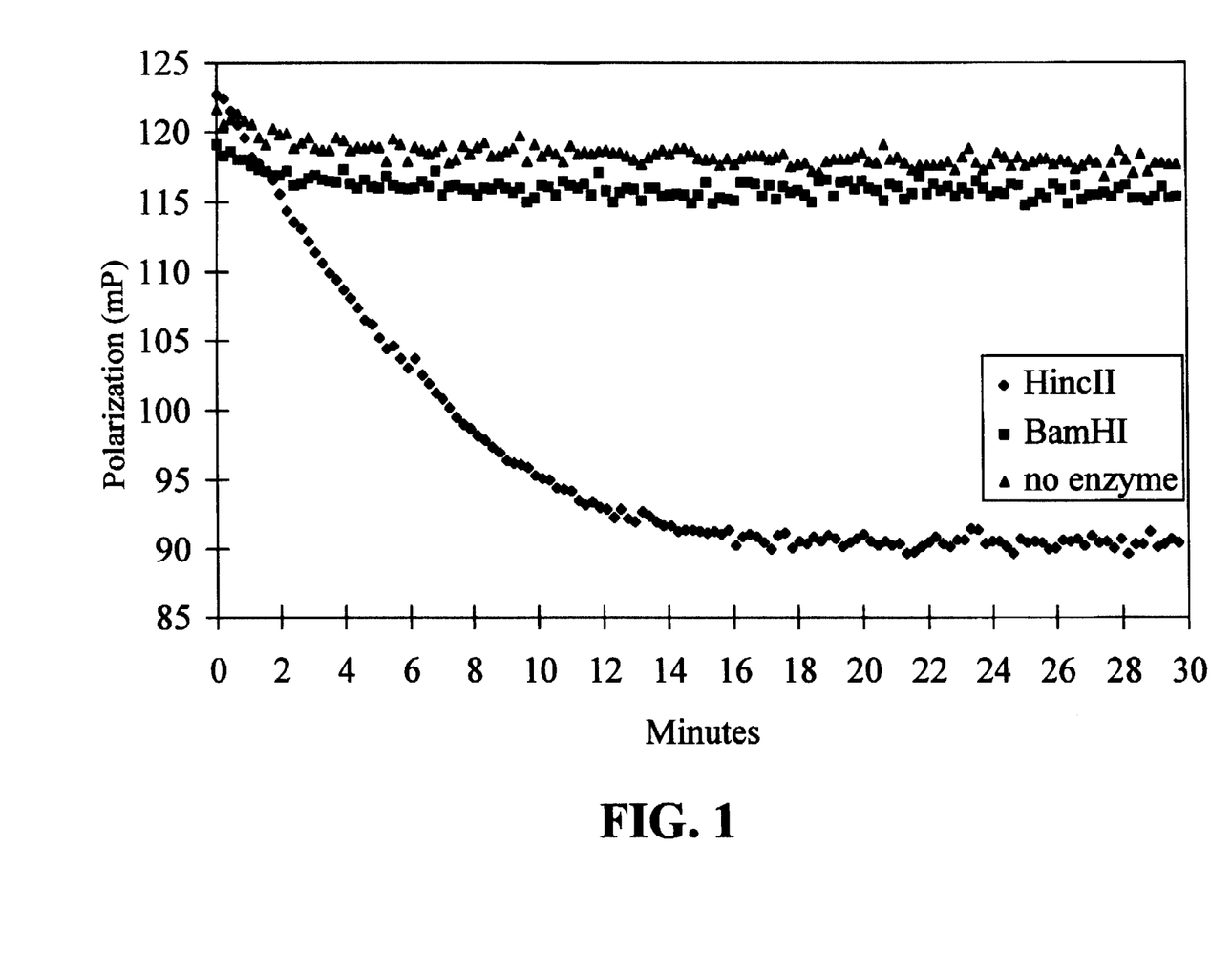
FIG. 1 is a graph illustrating FP detection of DNA cleavage by a restriction enzyme.

The 25 base-pair double stranded oligonucleotide was prepared by annealing the two strands in 1M NaCl, 10 mM potassium phosphate, 0.1 mM EDTA, pH 7.6. The mixture (10 uM) was heated together to 95 degrees for 10 minutes and slowly cooled to room temperature (20 minutes). 160 ng of the double stranded DNA was added to two 12×75 borosilicate tubes containing 1 ml of either BamH I or Hinc II restriction enzyme buffer (Takara Shuzo, Otsu, Japan). BamH I does not cleave the synthesized oligonucleotide. 20 units of the corresponding restriction enzyme was added to each tube and the reaction was heated at 37 degrees for 30 minutes. The fluorescence polarization of the reaction was measured every 13 seconds using the Beacon™ Fluorescence Polarization Instrument. A third tube contained 160 ng of the synthesized DNA and the buffer for Hinc II. This tube was incubated as a control with no enzyme added. Polarization values decreased due to Hinc II cleavage of the double-stranded DNA as illustrated in FIG. 1. No change in polarization was observed with either BamH I or with the control buffer.

EXAMPLE 2

F-DNA is incubated with a DNase I sample in assay buffer. DNase I activity in the sample cleaves F-DNA to smaller F-fragments and F-nucleotides. The change in polarization in the reaction tube is proportional to the total DNase I activity in the sample. The substrate is a 25 base pair, double-stranded, double 5' fluorescein labeled DNA specially designed to have a maximum change in fluorescence polarization from the intact to the fully degraded substrate.

The following substances and amounts were pipetted into 1.5 ml microcentrifuge tubes:

| REAGENT | BUFFER BLANK | SAMPLE BLANK | POSITIVE CONTROL | NEGATIVE CONTROL | SAMPLE TUBES |
|---|---|---|---|---|---|
| 5X Assay Buffer | 10 µl | 10 µl | 10 µl | 10 µl | 10 µl |
| DNase-free water | 40 µl | 10–34 µl | 28 µl | 30 µl | 0–29 µl |
| sample | | 1–30 µl | | | 1–30 µl |
| F-DNA | | | 10 µl | 10 µl | 10 µl |
| Positive Control | | | 2 µl | | |
| Total | 50 µl | 50 µl | 50 µl | 50 µl | 50 µl |

1) Fluorescein-DNA supplied by PanVera Corp., Madison, WI.
2) 5X Assay Buffer includes 125 mM Tris-HCl, pH 7.6; 25 mM MgCl$_2$; 0.25% Triton X-100 supplied by PanVera Corp., Madison, WI.
3) DNase Positive Control, DNase I in DNase Assay Buffer 1 mg/ml supplied by PanVera Corp., Madison, WI.
4) Deionized DNase-free Water, supplied by PanVera Corp., Madison, WI.
5) DNase Quench Buffer, 100 mM Tris-HCl pH 8.0; 5 mM MgCl$_2$, 0.5% SDS, 0.01% NaN$_3$, supplied by PanVera Corp., Madison, WI.

The reaction is stopped by adding each 50 µl reaction into test tubes containing 1 ml DNase Quench Buffer.

Read fluorescence polarization values in each reaction tube.

DNase I activity is identified by performing an endpoint assay. Each set of assays should include a "buffer blank" tube containing no substrate or DNase sample, and positive and negative control tubes. The negative control tube, containing only substrate, represents the starting polarization of the substrate. The positive control tube contains DNase I sufficient to completely degrade the substrate and therefore represents 100% degradation. The sample tubes contain substrate and the sample. All tubes are incubated for one hour at 37 C. Lower incubation temperatures may decrease the sensitivity, but may make the assay easier to perform. Longer incubation times (up to 18 hours) will increase sensitivity, but may also lead to increased background degradation of the substrate. The buffer blank is used to account for fluorescence background in the buffer. The polarization of the control and sample tubes is measured. A decrease in polarization in the sample tubes compared to the control tube indicates the presence of DNase I.

Figure 2:
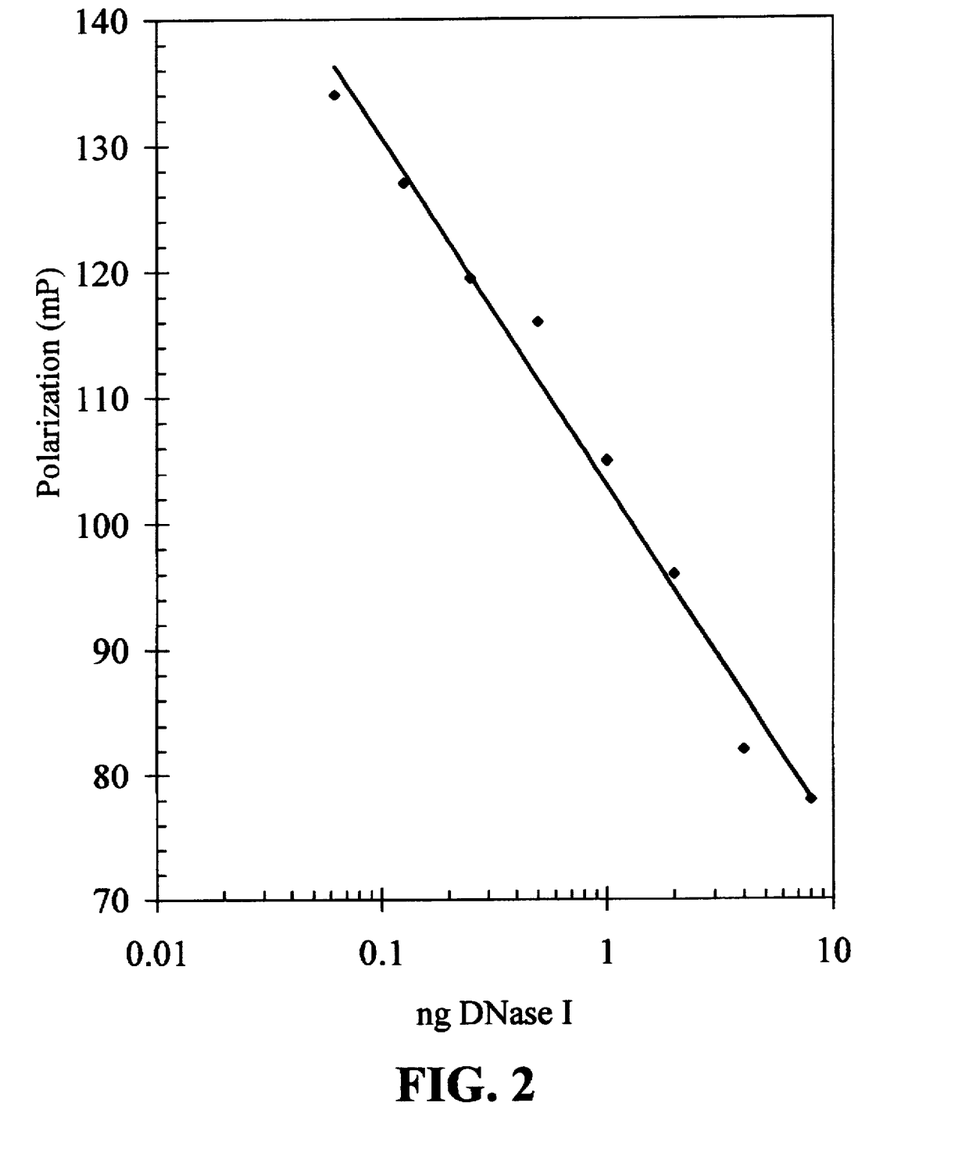
FIG. 2 is a graph illustrating the standard curve of DNase I activity.

DNase I activity is quantitated by developing a DNase standard curve that will be used to determine the range of DNase I concentrations that can be resolved. FIG. 2 illustrates a standard curve of DNase I activity. Various DNase I concentrations (0.5 pg to 500 pg) were added to reaction tubes containing F-DNA. A standard assay was performed with a 1 hour incubation at 37° C. Log DNase concentration was plotted vs. polarization (mP). The Beacon™ Fluorescence Polarization Instrument reports polarization values in mP (mP=1000×P). The line was constructed by linear regression.

EXAMPLE 3
Exonuclease III

Figure 5:
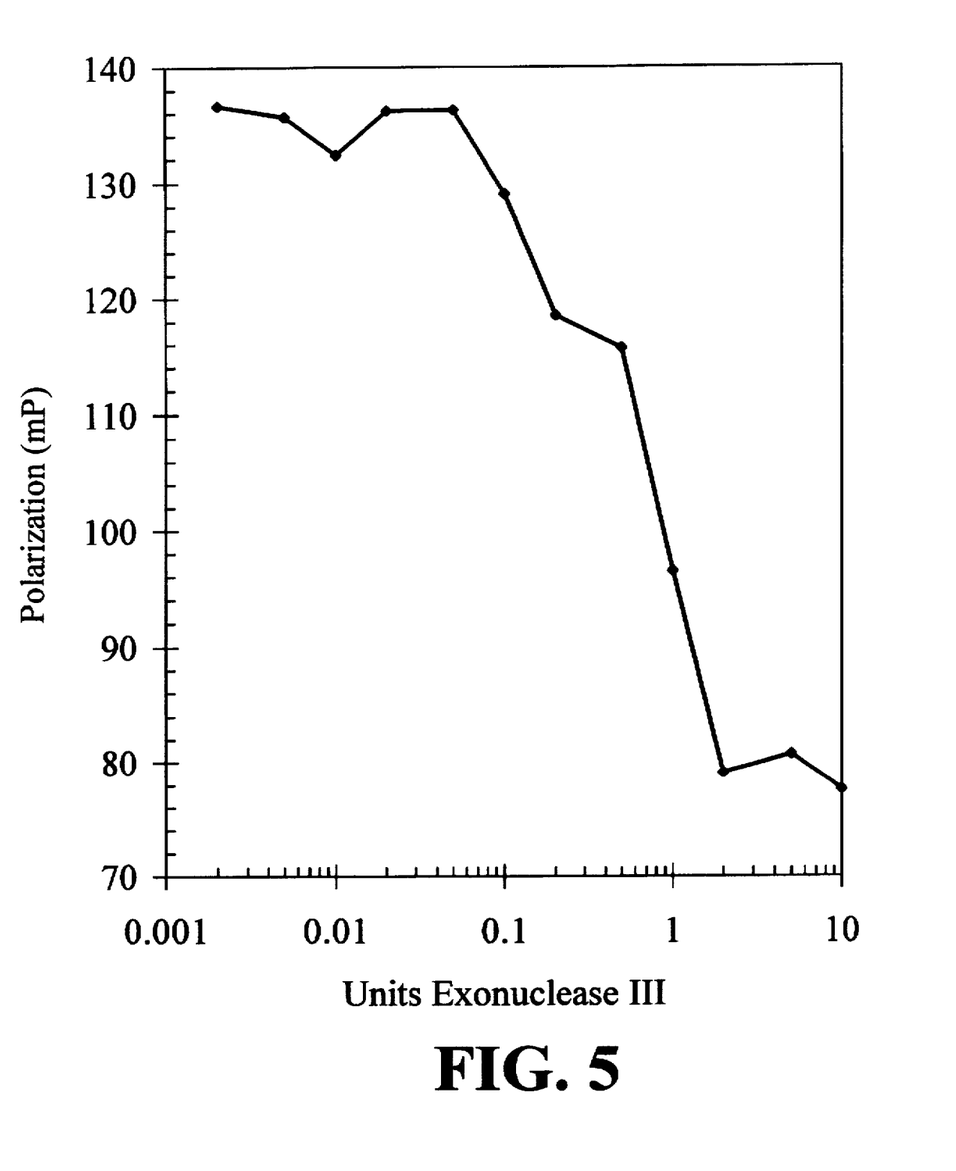
FIG. 5 is a graph illustrating enzyme cleavage of DNA by Exonuclease III.

The procedure is the same as EXAMPLE 2, except that Exonuclease III (New England Biolabs, Beverly, Mass.) is substituted for DNase I (see FIG. 5). Exonuclease III catalyzes the stepwise removal of mononucleotides from 3'-hydroxyl termini of duplex DNA. A limited number of nucleotides are removed during each binding event, resulting in coordinated progressive deletions within the population of DNA molecules. The enzyme is not active on single-stranded DNA and 3'-protruding termini are resistant to cleavage.

EXAMPLE 4
(RNase Cleavage of RNA)
Synthesis of fluorescein labeled RNA

Fluorescein labeled RNA was synthesized using T7 RNA polymerase in the following reaction: (all chemicals and reagents from Sigma Chemical, St. Louis, Mo., unless otherwise noted)
Add:
  80 µl 0.5M HEPES-KOH, pH 7.8
  6.0 µl 1.0M Magnesium chloride
  10 µl 100 mM spermidine
  20 µl 1.0M DTT
  50 µl 10 mM each GTP, CTP, ATP
  37.5 µl 10 mM UTP
  12.5 µl fluorecein labeled UTP (Boeringher Mannheim Biochemica, Indianapolis, Ind.)
  35 µl SspI digested pgem3 plasmid (15 ug) (Promega, Madison, Wis.)
  1.0 µl yeast pyrophosphatase
  30 µl T7 RNA polymerase 920 units/µl (Promega Corp., Madison, Wis.)
  118 µl RNase free water
Total:
  500 µl Incubate at 37 degrees C. for 2 hours. Add 20 µl T7 RNA polymerase and incubate for an additional 2 hours. Add 20 µl RQ DNase I (1 init/µl)(Promega, Madison, Wis.) and incubate at 37 degrees C. for 15 minutes. Purify the RNA by size exclusion chromatography using Sepacryl S-200 resin (Pharmacia, Milwaukee, Wis.) as per the vendors instructions. The concentration of the purified RNA is 0.13 µg/µl. F-RNA is incubated with a RNase sample in assay buffer.

RNase activity in the sample cleaves F-RNA to smaller F-fragments and F-nucleotides. The change in polarization in the reaction tube is proportional to the total RNase activity in the sample.

The following substances and amounts were pipetted into 1.5 ml microcentrifuge tubes:

| REAGENT | BUFFER BLANK | SAMPLE BLANK | POSITIVE CONTROL | NEGATIVE CONTROL | SAMPLE TUBES |
|---|---|---|---|---|---|
| 5X Assay Buffer | 20 µl | 20 µl | 20 µl | 20 µl | 20 µl |
| RNase-free water | 80 µl | 0–74 µl | 70 µl | 75 µl | 0–74 µl |
| sample | | 1–75 µl | | | 1–75 µl |
| F-DNA | | | 5 µl | 5 µl | 5 µl |
| Positive Control | | | 5 µl | | |
| Total | 100 µl | 100 µl | 100 µl | 100 µl | 100 µl |

1) Fluorescein-RNA supplied by PanVera Corp., Madison, WI.
2) 5X RNase Assay Buffer includes 125 mM Tris-HCl, pH 7.6; 25 mM MgCl$_2$; 0.25% Triton X-100 supplied by PanVera Corp., Madison, WI.
3) RNase Positive Control, RNase in RNase Assay Buffer 0.2 mg/ml supplied by PanVera Corp., Madison, WI.
4) Deionized RNase-free Water, supplied by PanVera Corp., Madison, WI.
5) DNase Quench Buffer, 100 mM Tris-HCl pH 8.0; 5 mM MgCl$_2$, 0.5% SDS, 0.01% NaN$_3$, supplied by PanVera Corp., Madison, WI.

The Buffer Blank is incubated along with Positive and Negative Control tubes and all Sample Tubes at 37 degrees C. for 1 hour.

The reaction is stopped by adding each 50 µl reaction into test tubes containing 1 ml RNase Quench Buffer.

Read fluorescence polarization values in each reaction tube.

RNase activity

RNase activity can be expressed in terms of a percent change in polarization using the following formula:

$$\% \Delta mP = \frac{(mP \text{ of negative control}) - (\text{sample } mP) \times 100}{(mP \text{ of negative control}) - (mP \text{ of positive control})}$$

mP of negative control represents the polarization of the substrate. mP of positive control represents the mP of the fully degraded product. Therefore, the denominator in the above reaction represents the maximum ΔmP possible. The numerator represents the measured ΔmP. For example, if the polarization of the negative control=100 and the positive control=30 and the test sample=60, then the percent change= {(100−60)/(100−30)}×100=57%.

Figure 3:
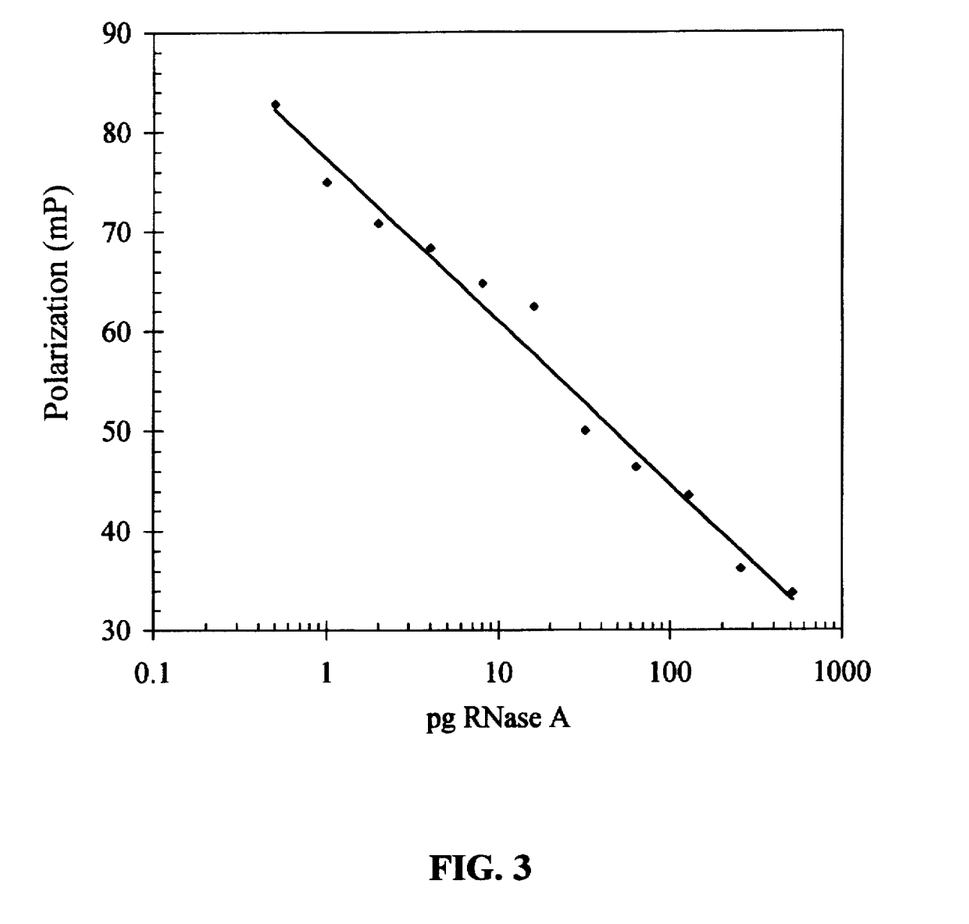
FIG. 3 is a graph illustrating the standard curve of RNase H activity.

RNase activity is quantitated by developing a RNase standard curve that will be used to determine the range of RNase concentrations that can be resolved. FIG. 3 illustrates a standard curve of RNase A activity. Various RNase concentrations (0.5 pg to 500 pg) were added to reaction tubes containing F-RNA. A standard assay was performed with a 1 hour incubation at 37° C. Log RNase concentration was plotted vs. polarization (mP). The Beacon™ Fluorescence Polarization Instrument reports polarization values in mP (mP=1000×P). The line was constructed by linear regression.

Examples of RNases that may be utilized with EXAMPLE 4 are:
  1) Ribonuclease A (RNase A) is derived from bovine pancreas. The enzyme is an endoribonuclease that specifically attacks pyrimidine nucleotides at the 3'-phosphate group and cleaves the 5'-phosphate linkage to the adjacent nucleotide. The end products are pyrimidine 3' phosphates and oligonucleotides with terminal pyrimidine 3' phosphates.

2) Ribonuclease T1 (RNase T1) which is an endoribonuclease that specifically attacks the 3'-phosphate groups of guanosine nucleotides and cleaves the 5'-phosphate linkage to the adjacent nucleotide. The end products are guanosine 3' phosphates and oligonucleotides with guanosine 3'-phosphate terminal groups.

EXAMPLE 5

Synthesis of cDNA for RNase H reaction

RNase H specifically cleaves the RNA strand of an RNA/DNA hybrid. This example demonstrates the utility of fluorescence polarization in measuring RNA cleavage in a RNA/DNA hybrid.

cDNA was synthesized from the fluorescein labeled RNA using the following conditions:
Add:

0.5 µl pGem 3z primer (5'-ATTGAAGCATTTATCAGGGT) (SEQ ID NO. 5) (0.6 ug)

8.0 µl fluorescein labeled RNA (from the prior section entitled: Synthesis of fluorescein labeled RNA) (1.0 ug)

2.5 µl deionized water

Heat to 70 degrees for 10 minutes

Chill on ice.

Add:

4 µl 5× 1st Strand Reverse Transcriptase Buffer (BRL, Gaithersburg, Md.)

2 µl 0.1M DTT

1 µl 10 mM dNTP's

Mix, centrifuge briefly.

Add:

1 µl Superscript Reverse Transcriptase (200 units/µl) (BRL)

Place at 37 degrees C. for 1 hour.

The product of this reaction was used directly in the next section without further purification.

RNase H Cleavage

Figure 4:
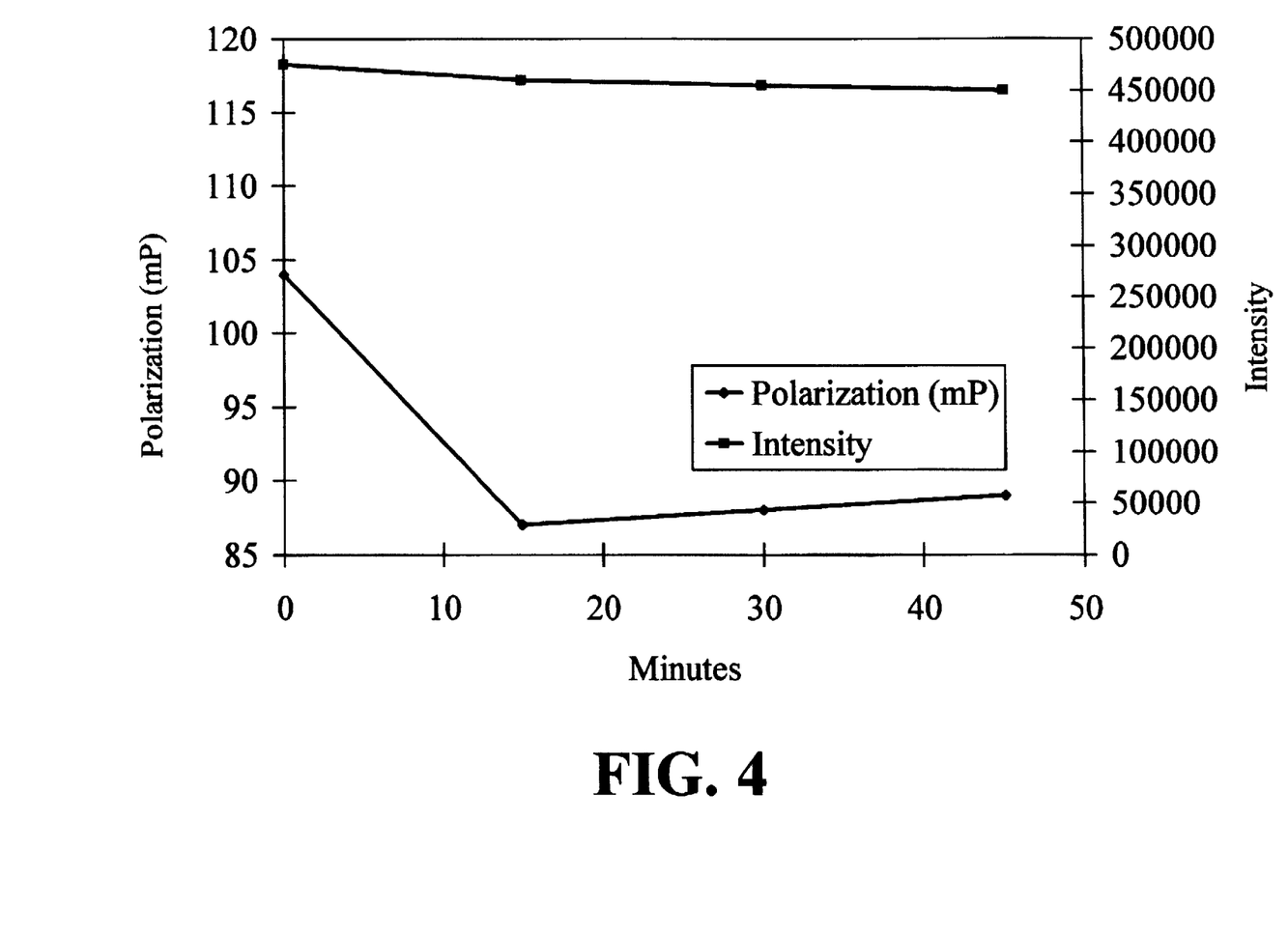
FIG. 4 is a graph illustrating FP detection of RNA cleavage by RNase H.

1 µl of RNA/DNA were incubated with 2.5 µl (1.5 units/µl) of ribonuclease H (Promega, Madison, Wis.) in 1 ml×RNase H buffer: 20 mM HEPES-KOH, pH 7.8, 50 mM KCl, 10 mM MgCl2 and 1 mM DTT. The polarization values were measured at 0, 15, 30, and 45 minute intervals. The fluorescence intensity was also measured at the same time points. FIG. 4 illustrates the cleavage of the fluorescein-labeled RNA in the RNA/DNA hybrid.

Ribonuclease H (RNase H) is a exoribonuclease which specifically degrades RNA in an RNA/DNA hybrid.

EXAMPLE 6

Description of Oligonucleotides used in DNase Assay

Several double-stranded oligonucleotides were tested in the DNase assay and one of the strands is described below. The complementary strand was also synthesized and the two were hybridized and used in the assay with DNase I and exonuclease III. The goal was to find DNA that gave the largest shift in polarization values (mP) between the DNA in intact form and cleaved form. Assume a single end label unless otherwise noted.

Trials performed on potential DNA oligonucleotides trpO-F, 25 mer, 5'end labeled on top strand

5'-ATC GAA CTA GTT AAC TAG TAC GCA A (SEQ ID NO. 1)

ERE-F, 50 mer, dual (top and bottom strand) 5' labeled

5'-GCA TCA GAT TAG AGC TGA TGC CTC CGG TCA CTG TCA CCC AAC CCA TCT TA (SEQ ID NO. 2)

PRE-F, 36 mer, 5'end labeled

5'-GAT CCT CGT TTT AAG AAC AGT TTG TAA CCA AAG ATC (SEQ ID NO. 3)

APREM6-F, 33 mer, 5' end labeled

5'-GAT CTC TGG TCA GGT TGT GAA ATC ACA ACT GTG (SEQ ID NO. 4)

PCR-amplified F-DNA

This last nucleic acid is a 100 bp amplicon (PCR fragment of DNA at the end of the reaction) amplified using 5'Fluorescein labeled primers, labeled on both top and bottom strands. This substrate performed poorly demonstrating very low intensity polarization readings. Contaminating unlabeled primers were most likely preferentially incorporated into the amplified DNA. This was rejected for low intensity and a lower mP than trpO-F, a much more economical substrate.

Our results indicate that trpO-f performs with the best results, showing the lagest change in polarization values between intact and cleaved DNA, providing the best results. Therefore, this DNA oligonucleotide is incorporated into the DNase assay described.

Double Stranded Oligonucleotide Sequences

ERE-F 27.8 mP (change in polarization)

PRE-F 6.6 mP (change in polarization)

SEQ ID NO: 2 F-DNA 36.6 mP (change in polarization)

trpO-F 54.8 mP (change in polarization)

APREM6-F 41.82 mP (change in polarization)

SEQ ID NO: 3

EXAMPLE 7

SEQ ID NO: 4

Protocol for Chemical Cleavage of Fluorescein-lableled RNA

Add 0.5 ul of purified Fl-RNA (described after RNA synthesis) to 1.0 ml of phosphate buffered saline solution.

Measure polarization value and intensity.

Add 1.0 ul of 5N sodium hydroxide, a non-nuclease chemical substance.

Measure polarization value and intensity.

|  | polarization value | fluorescence intensity |
|---|---|---|
| Fl-RNA | 110.1 | 358,807 |
| Fl-RNA (treated with NaOH) | 59.2 | 928,986 |

Protocol for Chemical Cleavage of Fluorescein-lableled RNA in an RNA/DNA Hydrid

Add 0.5 ul of purified Fl-RNA/DNA (taken directly from the cDNA reaction) to 1.0 ml of phosphate buffered saline solution.

Measure polarization value and intensity.

Add 1.0 ul of 5N sodium hydroxide.

Measure polarization value and intensity.

|  | polarization value | fluorescence intensity |
|---|---|---|
| Fl-RNA/DNA | 93.0 | 367,444 |
| Fl-RNA/DNA (treated with NaOH) | 60.5 | 629,745 |

The decrease in polarization represents the cleavage. The increase in intensity represents the fluorescence is quenched in the uncleaved state and when cleaved, emits more light.

The foregoing is considered as illustrative only of the principles of the invention. Further, since numerous modifications and changes will readily occur to those skilled in the art, it is not desired to limit the invention to the exact construction and operation shown and described. Therefore, accordingly, all suitable modifications and equivalents fall within the scope of the invention.

What is claimed is:

1. A method of detecting cleavage of a nucleic acid comprising:
   a) covalently attaching at least one fluorescence emitting label to a nucleotide of the nucleic acid to be cleaved;
   b) measuring the fluorescence polarization of the label before step c);
   c) incubating the labeled nucleic acid of step a) with a reagent to be tested wherein the reagent does not interact, in a manner that would diminish reagent activity enough to reduce useful sensitivity of cleavage measurement in step d), with the labeled nucleotide
   d) measuring the fluorescence polarization of the label during step c); and,
   e) comparing the fluorescence polarization measurements of step b) with step d).

2. The method of claim 1 wherein the fluorescence emitting label is selected from the group consisting of fluorescein, fluorescein derivatives and fluorescein analogs.

3. The method of claim 1 wherein the fluorescence emitting label is attached to the nucleic acid with a 1 to 21 carbon chain.

4. The method of claim 1 wherein the nucleic acid consists of DNA.

5. The method of claim 4 wherein the DNA consists of an oligonucleotide of between 2 and 50 bases.

6. The method of claim 4 wherein the DNA consists of two complementary oligonucleotides of between 2 and 50 base pairs each.

7. The method of claim 3 wherein the fluorescence emitting label is attached to an end of the oligonucleotide.

8. The method of claim 1 wherein the nucleic acid consists of an RNA strand.

9. The method of claim 8 wherein the fluorescence emitting label is attached periodically along the RNA strand.

10. The method of claim 1 wherein the nucleic acid consists of a DNA/RNA hybrid.

11. The method of claim 1 wherein measuring the fluorescence polarization consists of quantitative detection of polarized light emitted from the fluorescence emitting label.

12. A method of detecting cleavage of a nucleic acid comprising:
   a) covalently attaching a fluorescence emitting label to a nucleotide of the nucleic acid;
   b) measuring the fluorescence polarization of the label before step c);
   c) mixing a reagent to be tested with the labeled nucleic acid wherein the reagent does not interact, in a manner that would diminish reagent activity enough to reduce useful sensitivity of cleavage measurement in step e), with the labeled nucleotide
   d) incubating the mixture of step c) for a time sufficient for the reagent to react with the nucleic acid;
   e) measuring the fluorescence polarization of the label after step d); and,
   f) measuring the activity of the reagent by the degree of change in fluorescence polarization of the label.

13. The method of claim 12 wherein the fluoresence emitting label is from the group consisting of fluorescein, fluorescein derivatives and fluorescein analogs.

14. The method of claim 12 wherein cleavage is detected when the reagent of step (b) is a non-nuclease chemical substance.

15. The method of claim 12 wherein cleavage is detected when the reagent of step (b) is a nuclease.

16. The method of claim 12 wherein the label may be covalently attached to the reagent at one position or many positions.

* * * * *